United States Patent
Yasushi et al.

[11] Patent Number: 6,048,310
[45] Date of Patent: Apr. 11, 2000

[54] AUDIO APPARATUS

[75] Inventors: Mitsuo Yasushi; Masatoshi Yanagidaira; Jun Cheng; Kayoko Takashima; Hiroshi Satoh; Kazuyuki Uchiyama; Koji Watanabe, all of Tokyo, Japan

[73] Assignee: Pioneer Electronic Corporation, Tokyo, Japan

[21] Appl. No.: 09/226,167

[22] Filed: Jan. 7, 1999

[30] Foreign Application Priority Data

Mar. 2, 1998 [JP] Japan .................................. 10-066260

[51] Int. Cl.[7] ...................................................... A61B 5/00
[52] U.S. Cl. ........................... 600/300; 600/301; 128/905
[58] Field of Search .................... 600/300, 301, 600/595; 128/897, 898, 903, 904, 905, 920

[56] References Cited

U.S. PATENT DOCUMENTS

| | | | |
|---|---|---|---|
| 5,410,471 | 4/1995 | Alyfuku et al. | 600/300 |
| 5,441,047 | 8/1995 | David et al. | 600/300 |
| 5,544,649 | 8/1996 | David et al. | 600/300 |
| 5,600,305 | 2/1997 | Stafford et al. | 340/573 |
| 5,961,446 | 10/1999 | Beller et al. | 600/300 |

*Primary Examiner*—Max Hindenburg
*Assistant Examiner*—Navin Natnithithadha
*Attorney, Agent, or Firm*—Sughrue, Mion, Zinn, Macpeak & Seas, PLLC

[57] ABSTRACT

The audio apparatus of the invention has: vital information detecting means for detecting vital information of a resident; a database which is configured by information based on the vital information, and in which at least vital information of the resident is accumulated; audio signal information generating means for, when vital information is detected by the vital information detecting means, referring to the vital information of the database, and for generating predetermined audio signal information at the detection; and audio signal producing means for producing an audio signal to the resident, the audio signal being based on the audio signal information generated by the audio signal information generating means.

44 Claims, 6 Drawing Sheets

DATA AREA FOR ROOM 1

DATA AREA FOR ROOM 2

AUDIO APPARATUS

BACKGROUND OF THE INVENTION

The present invention relates to an audio apparatus which, in order to attain a comfortable psychological or physiological state desired by a person, judges a psychological or physiological state under the present environment on the basis of information from various sensors and personal information which are accumulated from the past, and, in order to create a comfortable environment desired by the person, generates various audio signals.

In Japan, an aged society is expected to proceed in the near future, and expansion of welfare facilities for aged persons, and a countermeasure for aged persons in home become social problems.

A nurse management system is known which is to be used in a hospital, an asylum for the aged, or the like. In the system, nurses and a nurse station are provided with a nurse call device having a display unit, a transmitter of a patient is connected to the nurse call devices by cable or wireless, so that the health and living states of the patient are managed.

Also for an aged person in home, a so-called emergency informing system is known in which, when the aged person suddenly has a fit or is taken ill, an emergency button or the like which is formed into a pendant-like shape is pressed in order to inform of this to a third party, with the result that this emergency state is notified to a neighbor or a local public entity through a telephone line.

The nurse management system and the emergency informing system have a main object of management of health of an aged person, and are vigorously developed as a nurse management apparatus. However, a facility or a system which is intended for provision of pleasantness to the life environment in daily life of an aged person is not widely used.

In an asylum for the aged or the like, for example, systems of a certain extent such as that light music is reproduced in a dining hall or an amusement hall, and that chimes ring on the time of lights-out are used. However, such systems are aimed at all residents including healthy persons and invalid aged persons who live in the asylum, and are not configured in consideration of physiological or psychological state of a resident.

Furthermore, the physiological state of a resident is affected and changed by time and the external environment. It is eagerly requested to attain widespread use of a general system which is configured in consideration of psychological or physiological state of a resident, and which can provide a resident with pleasantness.

SUMMARY OF THE INVENTION

The invention has been conducted in view of the above-discussed problems. It is an object of the invention to provide an audio apparatus in which data of vital information of each of residents are accumulated, and which can supply an audio signal optimum to physiological and psychological states of the resident, on the basis of the accumulated data and in accordance with the state of the resident (for example, whether the resident is sitting or not, or whether the resident is rising or not), and an action form of the resident (for example, movement or stillness of the person, presence or absence of utterance, presence or absence of working).

The audio apparatus of the invention comprises: vital information detecting means for detecting vital information of a resident; a database which is configured by information based on the vital information, and in which at least vital information of the resident is accumulated; audio signal information generating means for, when vital information is detected by the vital information detecting means, referring to the vital information of the database, and for generating predetermined audio signal information at the detection; and audio signal producing means for producing an audio signal to the resident, the audio signal being based on the audio signal information generated by the audio signal information generating means.

The audio apparatus set forth in aspect 2 comprises: a database in which, when a resident is in one of predetermined states, audio signal information corresponding to the state is accumulated for the state and for the resident; state detecting means for detecting a state of the resident; audio signal information generating means for, when the state of the resident is detected by the state detecting means, referring to the audio signal information of the database, and for generating predetermined audio signal information; and audio signal producing means for producing an audio signal to the resident, the audio signal being based on the audio signal information generated by the audio signal information generating means.

The audio apparatus set forth in aspect 3 comprises: vital information detecting means for detecting vital information of a resident; a database which is configured by information based on the vital information, and in which at least vital information of the resident and audio signal information are accumulated for each of the states and for the resident, the audio signal information corresponding to the state; audio signal information generating means for, when vital information is detected. by the vital information detecting means, referring to the vital information and the audio signal information of the database, and for generating audio signal information which is optimum in a state at the detection; and audio signal producing means for producing an audio signal to the resident, the audio signal being based on the audio signal information.

The audio apparatus set forth in aspect 4 is configured so that, in the audio apparatus according to any one of aspects 1 to 3, the apparatus further comprises action form detecting means for detecting an action form of the resident, and the audio signal information generating means generates audio signal information corresponding also to the action form which is detected by the action form detecting means.

The audio apparatus set forth in aspect 5 is; configured so that, in the audio apparatus of aspect 4, the action form detecting means detects whether one person exists in a room or plural persons exist in the room.

The audio apparatus set forth in aspect 6 is configured so that, in the audio apparatus of aspect 4, the action form detecting means detects whether a person in a room is still or moving.

The audio apparatus set forth in aspect 7 is; configured so that, in the audio apparatus of aspect 4, the action form detecting means detects whether a person in a room is conducting a predetermined work or not.

The audio apparatus set forth in aspect 8 is; configured so that, in the audio apparatus of aspect 4, the action form detecting means detects whether a person in a room is in an utterance state or not.

The audio apparatus set forth in aspect 9 is; configured so that, in the audio apparatus of aspect 1 or 3, the vital information detecting means includes a sensor attached to bedding, the sensor detects physiological data such as an electrocardiographic wave of the resident at sleeping, together with the physiological data, external data such as data of a date, a time, and weather when the physiological data are detected are accumulated in the database, physiological indices relating to physiological information of the resident at rising and sleeping are calculated on the basis of the accumulated data, and accumulated in the database, and feature amounts of the resident at rising and sleeping and obtained from the physiological indices are registered in the database.

The audio apparatus set forth in aspect 10 is configured so that, in the audio apparatus of aspect 9, the apparatus further comprises comparing means, the comparing means compares the physiological data at rising and sleeping and detected by the sensor, with the average physiological indices and feature amounts, and the audio signal information generating means generates audio signal information on the basis of a result of the comparison.

The audio apparatus set forth in aspect 11 is configured so that, in the audio apparatus of aspect 1 or 3, the vital information detecting means includes a sensor for detecting physiological data of the resident during action, physiological data of the resident during action are detected by the sensor, together with the physiological data, external data such as data of a date, a time, and weather when the physiological data are detected are accumulated in the database, physiological indices relating to average physiological information of the resident during action are calculated on the basis of the accumulated data, and accumulated in the database, and feature amounts of the resident during action and obtained from the physiological indices are registered in the database.

The audio apparatus set forth in aspect 12 is configured so that, in the audio apparatus of aspect 11, the apparatus further comprises comparing means, the comparing means compares the physiological data during action and detected by the sensor, with the physiological indices and feature amounts, and the audio signal information generating means generates audio signal information on the basis of a result of the comparison.

The audio apparatus set forth in aspect 13 is configured so that, in the audio apparatus of aspect 1 or 3, the vital information detecting means includes a sensor for detecting physiological data of the resident at rest, physiological data of the resident at rest are detected by the sensor, together with the physiological data, external data such as data of a date, a time, and weather when the physiological data are detected are accumulated in the database, physiological indices relating to physiological information of the resident at rest are calculated on the basis of the accumulated data, and accumulated in the database, and feature amounts of the resident at rest and obtained from the physiological indices are registered in the database.

The audio apparatus set forth in aspect 14 is configured so that, in the audio apparatus of aspect 13, the apparatus further comprises comparing means, the comparing means compares the physiological data at rest and detected by the sensor, with the physiological indices and feature amounts, and the audio signal information generating means generates audio signal information on the basis of a result of the comparison.

The audio apparatus set forth in aspect 15 is configured so that, in the audio apparatus of aspect 9, 11, or 13, the apparatus further comprises: means for calculating rhythm of variation relating to the resident, from the physiological data accumulated in the database; and comparing means for comparing a temporal change of physiological data obtained from the physiological data detected by the sensor, with the rhythm of variation, and the audio signal information generating means generates audio signal information on the basis of a result of the comparison.

The audio apparatus set forth in aspect 16 comprise: vital information detecting means for detecting vital information of a resident; audio signal producing means for producing plural audio signals of feature data and/or content data; selecting means for selecting a desired audio signal from the audio signal producing means; and a database in which, when the resident selects an audio signal through the selecting means, feature data and/or content data of the audio signal, and the vital information detected by the vital information detecting means are accumulated, and the audio signal producing means refers, when vital information of the resident is detected by the vital information detecting means, to the database, and produces an audio signal corresponding to the vital information.

The audio apparatus set forth in aspect 17 is configured so that, in the audio apparatus of aspect 16, when the resident selects a desired audio signal through the selecting means, external data such as data of a time and weather, and data relating to a state of the resident, and the state and vital information of the resident before and after the selection are accumulated in the database, and the audio signal producing means produces an audio signal which is optimum under a predetermined condition including the detected vital information.

The audio apparatus set forth in aspect 18 comprises: vital information detecting means for detecting vital information of a resident; audio signal producing means; for producing plural audio signals of feature data and/or content data; a database in which vital information which is detected by vital information detecting means of the resident when plural audio signals of feature data and/or content data are produced is accumulated together with the feature data and/or the content data; and learning means for referring to the database, and for learning an audio signal of optimum feature data and/or content data corresponding to vital information, and the audio signal producing means produces an audio signal of optimum feature data and/or content data obtained by the learning means, to the detected vital information.

The audio apparatus set forth in aspect 19 is configured so that, in the audio apparatus of aspect 18, external data such as data of a time and weather and data relating to a state of the resident when the plural audio signals of feature data and/or content data are produced and the state and vital information of the resident before and after the detection are accumulated in the database, the learning means refers to the database and learns an audio signal of optimum feature data and/or content data and corresponding to vital information, a time, weather, and the state of the resident before and after the detection.

The audio apparatus set forth in aspect 20 is configured so that, in the audio apparatus of aspect 10, the audio signal producing means produces the audio signal when the resident is to be induced to rise.

The audio apparatus set forth in aspect 21 is configured so that, in the audio apparatus of aspect 10, the audio signal producing means produces the audio signal when the resident is to be induced to sleep.

The audio apparatus of the invention comprises:
vital information detecting means for detecting vital information of a resident; a database which is configured by information based on the vital information, and in which at least vital information of the resident is accumulated; audio signal information generating means for, when vital information is detected by the vital information detecting means, referring to the vital information of the database, and for generating predetermined audio signal information at the detection; and audio signal producing means for producing an audio signal to the resident, the audio signal being based on the audio signal information generated by the audio signal information generating means. When vital information of a resident is detected, therefore, the apparatus can refer to the vital information of the resident, and supply an optimum audio signal to the resident.

Since the state detecting means for detecting the state of the resident is disposed, audio signal information which is to be supplied to the resident for each of the states and for the resident is accumulated. When the state of the resident is detected, therefore, the apparatus can refer to the audio signal information of the database, and supply an optimum audio signal corresponding to the state of the resident.

Since the action form detecting means for detecting an action form of the resident is disposed, the apparatus can, in the same manner as described above, supply an optimum audio signal corresponding to the action form of the resident, i.e., whether one person exists in a room or plural persons exist in the room, whether a person in a room is still or moving, whether a person in a room is conducting a predetermined work or not, or whether a person in a room is in an utterance state or not.

In the audio apparatus of the invention, the sensor attached to bedding is added to the vital information detecting means, and hence physiological data of the resident at sleeping can be detected by the sensor. Therefore, external data such as data of a date, a tire, and weather when the physiological data are detected are accumulated in the database, together with the physiological data, physiological indices relating to, physiological information of the resident at rising and sleeping are calculated on the basis of the accumulated data, and accumulated in the database, and feature amounts of the resident at rising and sleeping and obtained from the physiological indices are registered .ir the database. Consequently, it is possible to know relationships between the external environment and the physiological state of the resident.

Since the apparatus comprises the comparing means, the physiological data at rising and sleeping which are detected by the sensor can be compared with the physiological indices and feature amounts, and an optimum audio signal based on a result of the comparison can be supplied.

The vital information detecting means is provided with the sensor which detects physiological data of the resident during action or at rest. The sensor detects physiological data of the resident during action or at rest, external data such as data of a date, a time, and weather when the physiological data are detected are accumulated in the database, together with the physiological data, physiological indices relating to average physiological information of the resident during action or at rest are calculated on the basis of the accumulated data, and accumulated in the database, and feature amounts of the resident during action or at rest and obtained from the physiological indices are registered in the database. Consequently, it is possible to know relationships between the physiological state of the resident during action or at rest and the external environment.

Since the means for calculating rhythm of variation relating to the resident from the physiological data accumulated in the database is disposed, an optimum audio signal based on a result of a comparison between a temporal change of the physiological data of the resident and the rhythm of variation can be supplied.

The audio apparatus of the invention comprises: vital information detecting means for detecting vital information of a resident; audio signal producing means for producing plural audio signals of feature data and/or content data; selecting means for selecting a desired audio signal from the audio signal producing means; and a database in which, when the resident selects an audio signal through the selecting means, feature data and/or content data of the audio signal, and the vital information detected by the vital information detecting means are accumulated, and the audio signal producing means refers, when vital information of the resident is detected by the vital information detecting means, to the database, and produces an audio signal corresponding to the vital information. Therefore, the vital information of the resident and the desired audio signal selected by the selecting means can be accumulated in the database with being correlated with each other.

Since the apparatus comprises the learning means for learning an audio signal of feature data and/or content data, it is possible to supply an audio signal of optimum feature data and/or content data. When also external data such as the time and the weather are accumulated in the database, it is possible to supply an audio signal of optimum feature data and/or content data which corresponds to the vital information, the time, the data, the weather, the state of the resident, and the state of the resident before and after the detection.

DETAILED DESCRIPTION OF THE PREFERRED EMBODIMENTS

Figure 1:
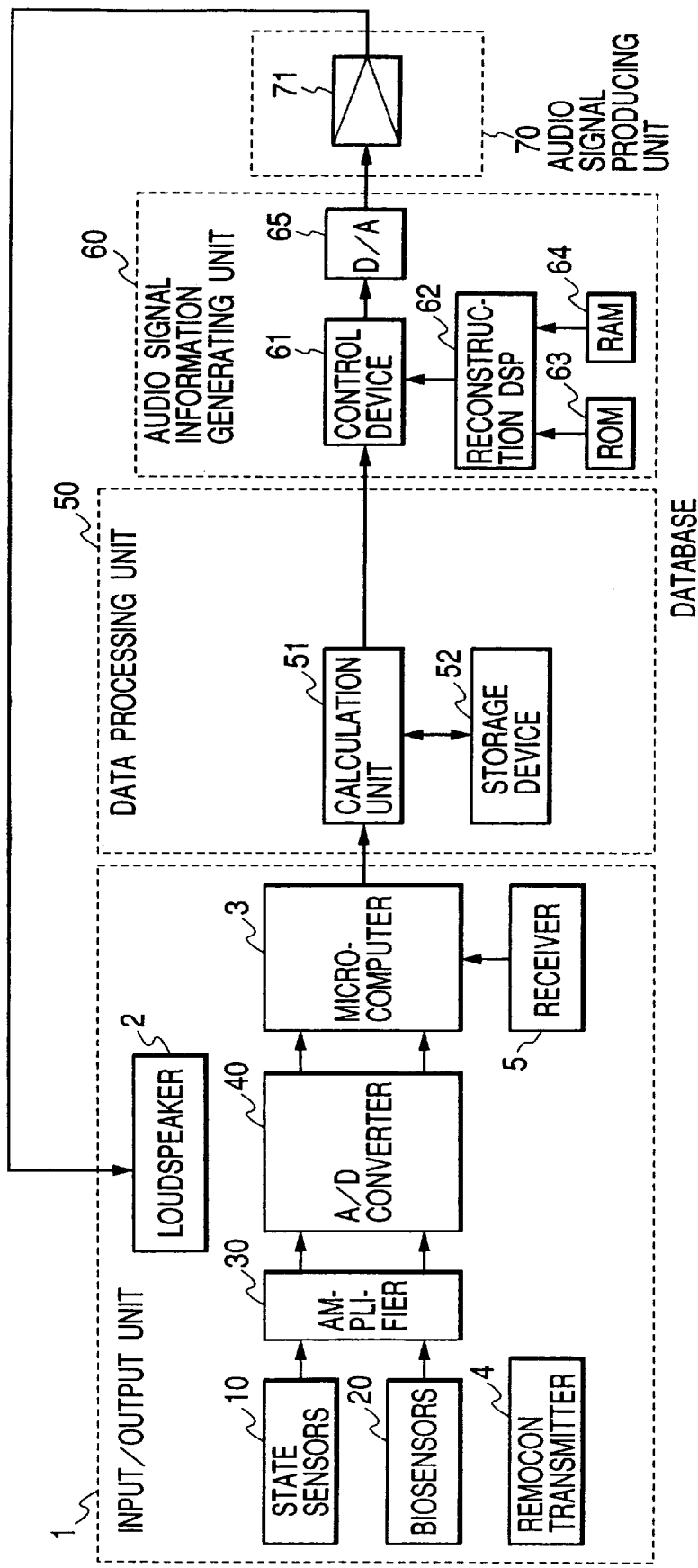
FIG. 1 is a block diagram of an audio apparatus of a first embodiment of the invention.

Hereinafter, the configuration and operation of an audio apparatus of a first embodiment of the invention will be described in detail with reference to FIGS. 1 to 3. FIG. 1 is a block diagram of the audio apparatus of the first embodiment of the invention, FIG. 2 is a block diagram showing various state sensors and biosensors which are used in the audio apparatus, and FIG. 3 is a data map of a storage area of a database which is used in the audio apparatus.

The audio apparatus of the invention is disposed in, for example, an asylum for the aged. As shown in FIG. 1, the apparatus comprises: input/output units 1 having various sensors and a loudspeaker and respectively placed in rooms; a data processing unit 50 which processes digital data supplied from the input/output units 1; an audio signal information generating unit 60 which generates an audio signal information; and an audio signal producing unit 70 which produces an audio signal. The components other than the input/output units 1 in the rooms are centrally controlled in a control room which is disposed at another place.

Each of the input/output units 1 respectively placed in the rooms has: various state sensors 10 which are state detecting means for detecting the state of a resident; various biosensors 20 which are vital information detecting means for detecting vital information of a resident; amplifiers 30 which amplify output signals supplied from the state sensors 10 and the biosensors 20; and A/D converters 40 which convert analog signals supplied from the amplifiers 30 into digital signals. The digital signals of the A/D converters 40 are supplied to a microcomputer 3.

In each of the rooms, disposed are a loudspeaker 2 which outputs an audio signal, a remote-control transmitter 4 which is used for registering a room number, a resident number, and sensor numbers and switching to a desired audio signal, and a remote-control receiver 5.

Figure 2A:
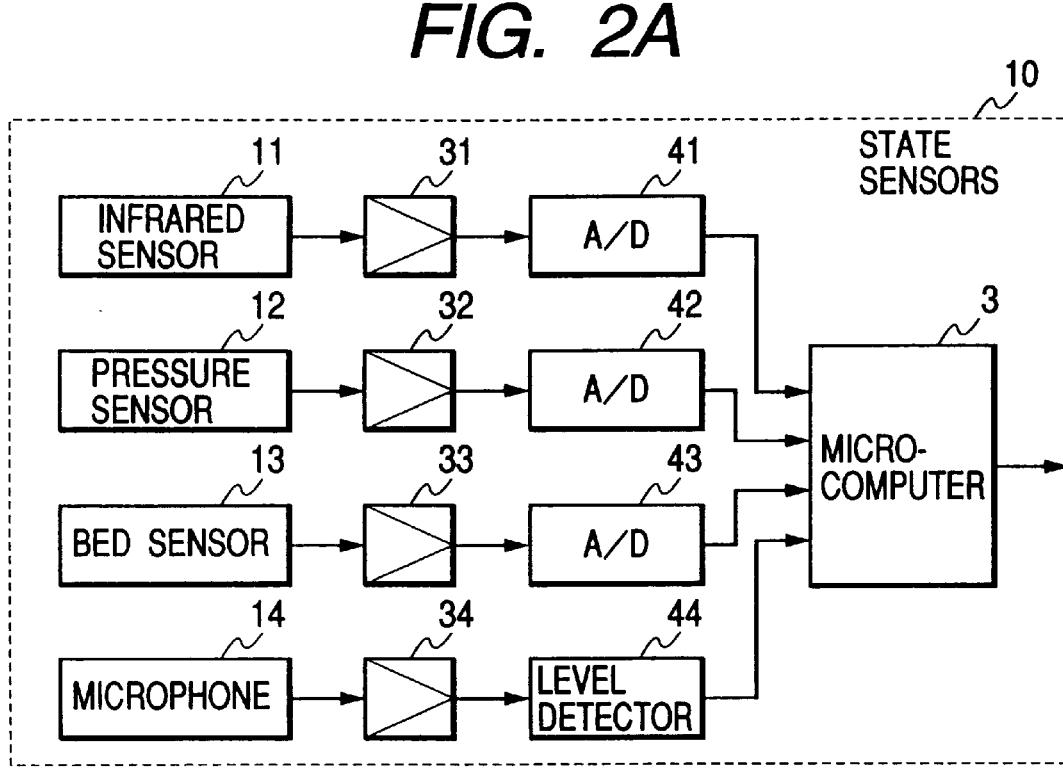
FIGS. 2A and 2B are block diagram showing various state sensors and biosensors which are used in the audio apparatus of the invention.

FIG. 2 shows the configuration of the state sensors 10 and the biosensors 20 which are disposed in each of the rooms. The state sensors 10 shown in FIG. 2A are disposed for detecting the state of a resident, for example, whether the resident is in the room, lying in bed, sitting in a chair or on the floor, or walking, and configured by infrared sensors 11, pressure sensors 12, a bed sensor 13, a microphone 14, etc.

For example, plural infrared sensors 11 may be placed at different heights from the floor, so that the state of a resident, i.e., whether the resident is sitting or standing can be detected. When the microcomputer 3 calculates the level relationship among output signals from plural infrared sensors 11 disposed at various places of the room, it is possible to detect whether the resident is walking or not.

When plural pressure sensors 12 are disposed in a carpet, it is possible to detect the position of the resident in the room. When a pressure sensor 12 is disposed in a chair, it is possible to detect the state of sitting in the chair, and, when the bed sensor 13 is disposed in a bed, it is possible to detect whether the resident is sleeping or not. In the case where it is required to detect the presence of the resident in the room by means of sound, the detection is enabled by disposition of the microphone 14.

The output signals from the state sensors 10 are amplified by amplifiers 31 to 33 which are disposed for the sensors, respectively. The analog signals are converted by A/D converters 41 to 43 into digital signals and then supplied to the microcomputer 3.

The output signal of the microphone 14 is similarly amplified by an amplifier 34, converted into a digital signal consisting of ON and OFF levels by a level detector 44, and then supplied to the microcomputer 3. When the presence or absence of the resident in the room is detected depending on the level of a sound, the output signal can be treated in the form a digital signal in the same manner as the output data of the A/D converters 41 to 43 for the other sensors.

In the case where the output signal of the microphone 14 must be directly processed, the following configuration may be employed. After the output signal of the microphone 14 is amplified, the amplified signal is supplied by cable to a wave analyzer (not shown) in the data processing unit 50 which is centrally controlled in the control room. Digital data output from the wave analyzer are supplied to a calculation unit 51 in the data processing unit 50.

The digital data output from the wave analyzer may be used in analyzation of the voice frequency band and the frequency spectrum for each resident. Such analyzation is conducted in identification of a resident which will be described later.

Figure 2B:
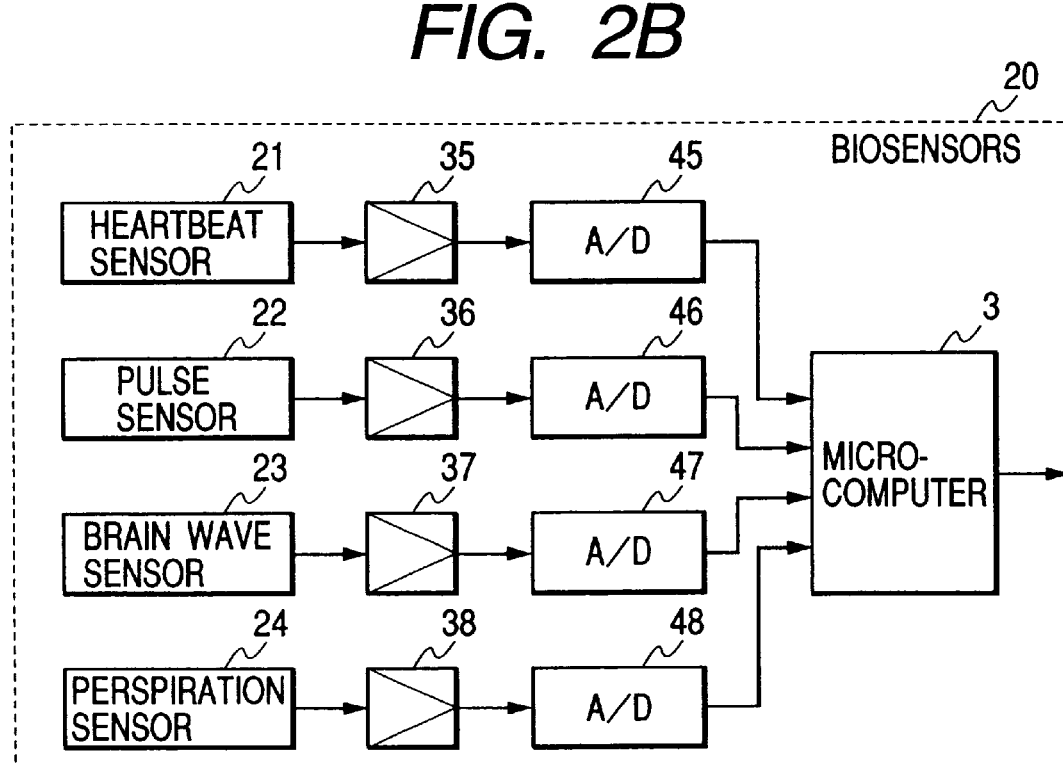
Figure 3A:
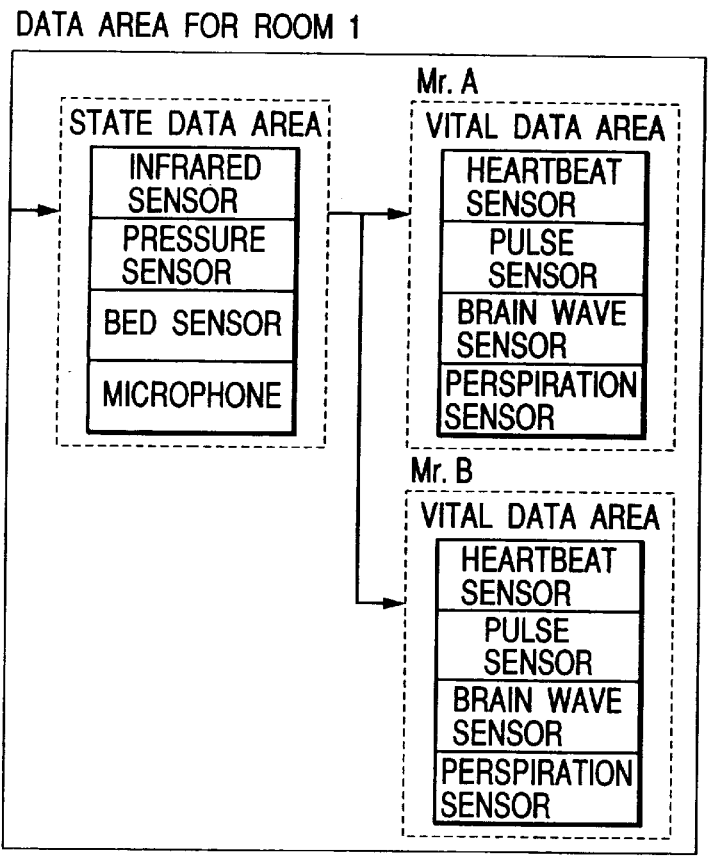
FIGS. 3A and 3B are data map of a storage area of a database which is used in the audio apparatus of the invention.
Figure 3B:
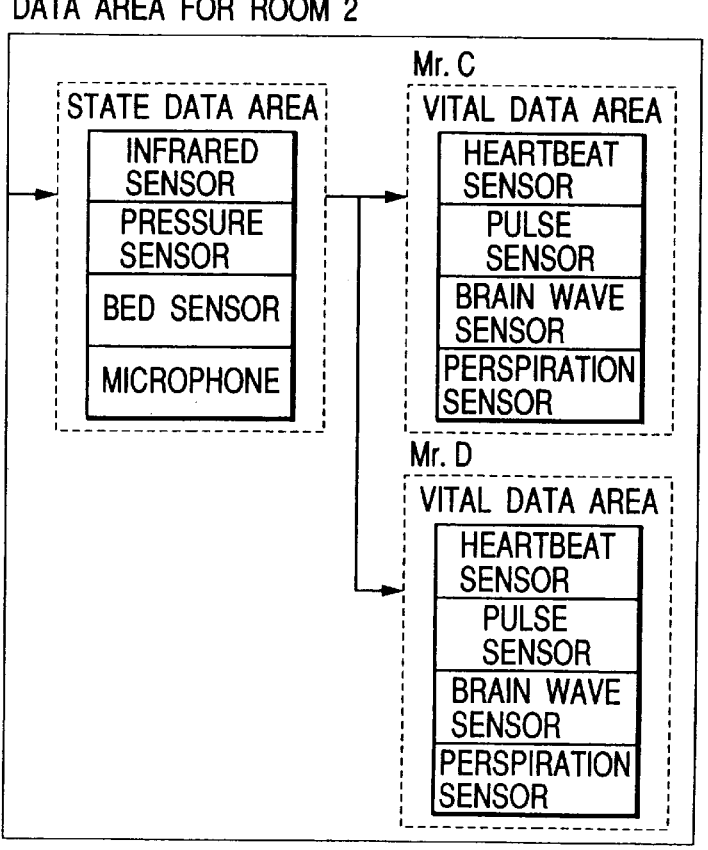

The biosensors 20 shown in FIG. 2B are disposed for detecting the physiological state of the resident, and configured by a heartbeat sensor 21, a pulse sensor 22, a brain wave sensor 23, a perspiration sensor 24, etc.

When the resident is in an invalid state, the physiological state of the resident can be always detected by the following configuration. The biosensors 20 are attached to sites of the body of the resident. The output signals from the biosensors 20 are connected through cables to amplifiers 35 to 38 to be amplified, and then digital signals are supplied via AID converters 45 to 48 to the microcomputer 3.

By contrast, when the resident is a healthy person, cables for the biosensors 20 attached to the resident nay impede the walking, and hence cables of required ones of the biosensors 20 are connected to, for example, a portable transmitter.

The portable transmitter may be an infrared transmitter which amplifies the output signals from the biosensors 20, converts the amplified signals into digital signals, and then modulates infrared rays in the form of FSK or the like. According to this configuration, the infrared rays can be received by the remote-control. receiver 5 which is disposed in the room, and the output signals can be handled in the same manner as the digital signals of the other sensors.

The output signals from the biosensors 20 are amplified by the amplifiers 35 to 38 which are respectively disposed for the sensors, and the amplified analog signals are converted into digital signals by the A/D converters 45 to 48 and then supplied to the microcomputer 3.

The microcomputer 3 adds the sensor number, the resident number, and the room number which are previously set, to the digital signals of the A/D converters 41 to 48, and converts the digital signal of the level detector 44 into a digital data to which the room number is added. These digital data are then supplied by cable or wireless to the data processing unit 50 in the control room.

The data processing unit 50 consists of the calculation unit 51 and a storage device 52 so as to constitute a database in which digital data output from the microcomputers 3 of the rooms are hierarchically classified and accumulated. The storage device 52 is configured by a RAM which temporarily stores processed digital data, a large-capacity HDD, etc.

In the case where the resident has been registered, the digital data output from the microcomputer 3 are always supplied to the data processing unit 50. The data processing unit 50 judges whether the obtained digital data are to be processed continuously or in the unit of time.

The digital data supplied to the data processing unit 50 are stored in areas of the storage device 52 which are ensured for the room numbers, the resident numbers, and the sensor numbers which are added to the digital data in the calculation unit 51.

As shown in FIG. 3, the data areas of the storage device 52 are formed as hierarchies for each room. In the data area for room 1, for example, state data detected from the state sensors 10 are sequentially stored into the state data area for room 1. In the lower hierarchy, sequential vital information detected from the biosensors 20 of, for example, Messrs. A and B, and average vital information of the residents which is obtained by processing the vital information and the state data in the calculation unit 51 with being correlated with the state data (or vital information at a normal state, feature vital information, and the like, and hereinafter such information is referred to as average vital information) are stored into a vital data area for each person.

In the data area for room 2, similarly, state data detected from the state sensors 10 are sequentially stored into the state data area for room 2. In the lower hierarchy, vital information detected from the biosensors 20 of, for example, Messrs. C and D, and average vital information of the residents which is obtained by processing the vital information and the state data in the calculation unit 51 with being correlated with the state data are stored into a vital data area for each person.

On the basis of the state data supplied from the rooms, the calculation unit 51 refers the average vital information for each person which is already stored, and, outputs a control signal to the audio signal information generating unit 60 in order to generate audio signal information which is optimum to the state of a resident, and stores and accumulates the audio signal information as data correlated with respective state data, into the storage device 52.

The control signal output from the data processing unit 50 is supplied to the audio signal information generating unit 60 which serves as the audio signal information generating means.

The audio signal information generating unit 60 is configured by, for example, a MIDI source and a control device 61, and can generate various audio signals, pseudo sound, etc. A reconstruction DSP 62 processes waveform data read out from a waveform data ROM 63 and a waveform data RAM 64 to convert the data into acoustic data. The waveform data ROM 63 stores waveform data of basic audio signals, and the waveform data RAM 64 stores waveform data which are contained in music piece data but are not basic ones.

When the data of the waveform data ROM 63 and the waveform data RAM 64 are read out to the reconstruction DSP 62 to be processed and the digital signals are converted into analog signals, various audio signals, pseudo sound, and the like can be generated.

In accordance with the control signal from the calculation unit 51, the control device 61 reads out waveform data required for generation of predetermined audio signal information, from waveform data which are previously stored in the waveform data ROM 63, and those which are stored in the waveform data RAM 64, into the reconstruction DSP 62, and processes the read out waveform data. Thereafter, the digital signal is converted into an analog signal in a D/A converter 65, and the analog signal passes through a filter which is not shown, whereby a predetermined audio signal is generated.

The audio signal output from the audio signal information generating unit 60 is supplied to the audio signal producing unit 70 to be amplified by an amplifier 71. The amplified signal is supplied to the loudspeaker 2 of each room.

Next, the operation of the audio apparatus of the first embodiment of the invention will be described with; reference to the case where Mr. A of room 1 is lying on the bed so as to sleep.

When Mr. A lies on the bed, the bed sensor 13 detects the weight of Mr. A, and the output signal of the bed sensor 13 is supplied to the microcomputer 3 via the amplifier 33 and the A/D converter 43. When Mr. A wears the brain wave sensor 23 by means of a headband or the like, the output signal of the brain wave sensor 23 is supplied to the microcomputer 3 via the amplifier 37 and the A/D converter 47. The microcomputer 3 adds the sensor number, the resident number of Mr. A, and the room number to the digital signal from the bed sensor 13, and supplies the resulting data to the data processing unit 50 as the state data of Mr. A. Furthermore, the microcomputer adds the sensor number, the resident number of Mr. A, and the room number to the digital signal from the brain wave sensor 23, and supplies the resulting data to the data processing unit 50 as physiological information of Mr. A.

The calculation unit 51 of the data processing unit 50 stores the state data detected from the bed sensor 13, into the state data area for room 1, and the vital information detected from the brain wave sensor 23 of Mr. A, into the lower hierarchy. The calculation unit 51 processes the vital information and the state data, and stores average vital information of Mr. A with being correlated with the state data, into the personal vital data area.

Furthermore, the calculation unit 51 operates in the following manner. When state data and vital information are detected, the past average vital information of Mr. A which is stored in the storage device 52 is read out, and audio signal information is extracted from average vital information which is closest to the currently detected state data and vital information. The control signal is sent to the audio signal information generating unit 60 so as to generate the audio signal information. The audio signal information is correlated with this state data, and then stored and accumulated into thus storage device 52, as, for example, audio signal information of the sleeping state of Mr. A.

On the basis of the control signal supplied from the calculation unit 51, the audio signal information generating unit 60 reads out waveform data required for generation of predetermined audio signal information, from waveform data which are previously stored in the waveform data ROM 63, and those which are stored in the waveform data RAM 64, into the reconstruction DSP 62, and processes the read out waveform data. Thereafter, the digital signal is converted into an analog signal in the D/A converter 65, whereby, for example, an audio signal of the sleeping state of Mr. A is generated.

For example, the audio signal of the sleeping state is set to a signal which induces the α wave that, when a person is in a quiet sleep state, is largely generated from the brain. The audio signal for sleeping and output from the audio signal information generating unit 60 is supplied to the audio signal producing unit 70 serving as audio signal producing means, to be amplified by the amplifier 71. The amplified signal is output from the loudspeaker 2 of room 1.

The loudspeaker 2 of room 1 outputs the audio signal for sleeping so as to induce Mr. A sleeping on the bed to a quiet sleep state.

The brain wave sensor 23 attached to the resident detects the α wave generated from the brain.

The microcomputer 3 supplies digital data in which the sensor number, the resident number, and the room number are added to the detected vital information of the brain wave sensor 23 of Mr. A and the state data of the bed sensor 13, to the data processing unit 50.

The calculation unit 51 of the data processing unit 50 stores the state data of the bed sensor 13 into the state data area for room 1, and the vital information of the brain wave sensor 23 correlated with the state data is stored into the vital data area for Mr. A.

The calculation unit 51 of the data processing unit 50 compares the currently obtained vital information with the vital information of the brain wave sensor 23 which was generated when Mr. A was in a quiet sleep state. If the resident must be induced to a more quiet sleep state, audio signal information corresponding to the state is accumulated for the state and for the resident, in the database. The calculation unit refers average vital information accumulated in the database, and outputs the control signal to the audio signal information generating unit 60 so as to output predetermined audio signal information. In response to the control signal, the audio signal information generating unit 60 outputs an audio signal which is prepared for inducing a resident to a quiet sleep state. The signal is supplied to the audio signal producing unit 70 to be amplified by the amplifier 71. The amplified signal is output from the loudspeaker 2 of room 1.

Therefore, the data processing unit 50 can refer current personal state data and vital information of a resident which are always supplied, and, if the average vital information accumulated in the database is in a predetermined state, can provide the resident with an audio signal corresponding to the predetermined state.

As sound inducing to a quiet sleep state, in addition to the signal inducing the α wave, used is an audio signal which gives an impression of "quiet sound" to many residents, such as sound of the murmur of a brook, sound of ripples, or a music piece of a slow tempo and particularly favored by the residents.

The above described state sensors 10 can be used as action form detecting means for detecting that plural residents are conducting operations in a room such as an amusement hall, or are in an utterance state.

For example, it is possible to judge that plural residents are in a room, under conditions including the followings.

1) From output signals of sensors (the infrared sensors, the pressure sensors, and the like) in a room, it is estimated that one or more residents exist in the room, and plural positions of residents are estimated from the output signals of the infrared sensors or the pressure sensors.

2) From output signals of sensors in a room, it is estimated that one or more residents exist in the room, and positions of residents which are estimated from the output signals of the infrared sensors or the pressure sensors spread over a range which is wider than a predetermined area (in other words, an estimated position of a resident cannot be narrowed to a specific position).

3) From output signals of sensors in a room, it is estimated that one or more residents exist in the room, and positions of residents which are estimated from the output signals of the infrared sensors or the pressure sensors are changed at a frequency which is higher than a predetermined value (the movement is so rapid that it cannot be considered that one resident is moving around).

Furthermore, it is possible to judge that a resident is moving in a room, under conditions including the followings.

4) The changing amount and rate (or the frequency) of a vertical pressure applied to the pressure sensors disposed in the floor is within a predetermined range.

5) The moving rate of the position of a resident. estimated from the outputs of the sensors in the room is within a predetermined range.

6) The output of the microphone in the room contains a signal indicative of a feature (variation of the is frequency spectrum or the sound pressure level, or the like) of walking of a resident.

Moreover, it is possible to judge that a resident in the room is conducting a work of some kind, under conditions including the followings.

7) A movement of a person is detected within a predetermined time period and at a frequency which is higher than a predetermined value.

8) A sensor for a tool such as a cooking tool or a cleaning tool which is to be actively used by a resident is outputting a signal indicative of the use of the tool, and there is no information indicative of an abnormality of the tool.

9) An air conditioner, an AV apparatus, or the like which is to be passively used by a resident is operated within a predetermined time period and at a frequency higher than a given value.

10) In the output signal of the microphone disposed in the room, the changing amount and rate (or the frequency) of the level and the frequency spectrum are greater than a predetermined value, and there is no information indicative of an abnormality.

Moreover, it is possible to judge that a resident in the room is talking, under conditions including the followings.

11) In the frequency spectrum of the voice frequency ban-d (about 300 to 3,000 Hz) and the pattern of the level variation (temporal change) of a signal which is obtained by removing sound produced by an AV apparatus, or a game machine from the output signal of the microphone disposed in the room, there is a feature of utterance of a resident.

The action form data detected by the action form detecting means are supplied from the amusement hall to the data processing unit 50, in the form of digital data to which the number of the amusement hall is added.

The data processing unit 50 accumulates the action form data of the amusement hall in the database, refers average vital information corresponding to the action form data, and outputs the control signal to the audio signal information generating unit 60 in order to output a predetermined audio signal.

On the basis of the obtained action form data, the data processing unit 50 extracts audio signal information corresponding to the action state at that time, such as conversation in the amusement hall, or working, and outputs the control signal to the audio signal information generating unit 60 in order to generate an audio signal corresponding to conversation or working in the amusement hall. On the basis of the control signal from the data processing unit 50, the audio signal information generating unit 60 generates audio signal information and supplies the information to the audio signal producing unit 70. The signal of the audio signal producing unit is amplified by the amplifier 71, and then output from the loudspeaker 2 disposed in the amusement hall.

The action form detecting means conducts not only the detection of the action form of a resident, but also the following operations. When a resident uses a sound producing medium such as a game, a CD, or broadcasting, the wave analyzer analyzes features of the sound (for example, the pattern of the level variation, rhythm, tempo, frequency spectrum, and pitch variation) . The features are accumulated in the database, together with the time, the weather, the physiological state, and contents of the action at this timing, and actions and the physiological state before and after the analyzation. On the basis of the accumulated data, probabilities that which kind of sound is often listened under a certain situation (the time, the weather, the physiological state, contents of the action, and the number of persons in the amusement hall), or after a certain situation are calculated. The calculated probabilities are accumulated in the database, as information of sounds which are personally favored by the resident.

In the case where information indicative of contents (the kind of sound, the person producing the sound, the name of the music piece, contents of a talk, the words, and the like) supplied from a medium used by the resident are output together with the sound, the contents are accumulated in the database, together with the time, the weather, the physiological state, and contents of the action at this timing, and actions and the physiological state thereafter. On the basis of the accumulated data, probabilities that which kind of sound is often listened under a certain situation (the time, the weather, the physiological state, contents of the action, and the number of persons in the amusement hall), or after a certain situation are calculated. The calculated probabilities are accumulated in the database, as information of sounds which are personally favored by the resident.

Alternatively, state sensors and action form sensors may be disposed in a toilet room and a bathroom in addition to the amusement hall and the private rooms. In the alternative, even when a resident is in any room, the action form and the physiological state of the resident can be observed and an audio signal which provides the living environment of the resident with pleasantness and comfortableness can be always supplied.

Figure 4:
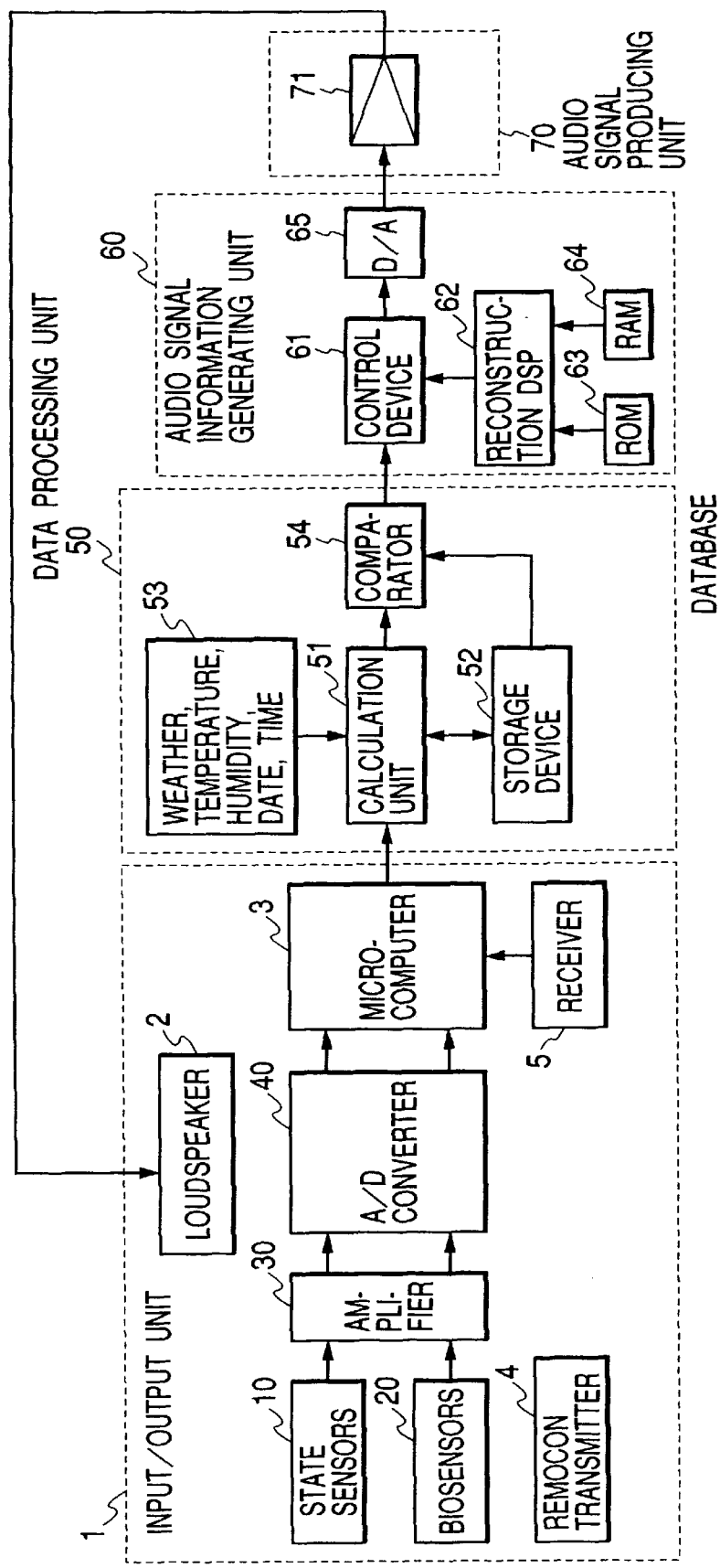
FIG. 4 is a block diagram of an audio apparatus of a second embodiment of the invention.

FIG. 4 is a block diagram of an audio apparatus of a second embodiment of the invention.

In the audio apparatus of the second embodiment, the above-described audio apparatus of the first embodiment is modified so that the data processing unit of the audio apparatus captures external data including the date, the time, and the weather (temperature and humidity), and the apparatus further comprises comparing means for comparing obtained state data and vital information with average vital information. Hereinafter, a process of physiological data of a resident at rising and sleeping will be particularly described.

The data processing unit 50 of the audio apparatus captures weather data such as the temperature, the humidity, and the atmospheric pressure, and data such as the date and the time which are detected from a timer, and accumulates these data in the database, as external data.

As described above, the bed sensor 13 and the perspiration sensor 24 are disposed in a bed of a resident, and, as required, the heartbeat sensor 21, the pulse sensor 22, and the like are attached to the body of the resident. When the resident lies on the bed, therefore, state data and vital information from the state sensors 10 and the biosensors 20 are sent to the data processing unit 50.

The calculation unit 51 of the data processing unit 50 stores the various vital information of residents at rising and sleeping supplied from each of the rooms, into the areas of the storage device 52 which are secured for each of the room numbers, the resident numbers, and the sensor numbers. In this case, the vital information is stored with being correlated with the external data, as physiological data.

As described above, vital information of a resident in the daytime is accumulated in the database as average vital information. Therefore, the calculation unit 51 calculates average physiological indices on the basis of, for example, vital information of the resident obtained at sleeping and average physiological information, and accumulate the indices in the database with being correlated with the external data. In this way, feature amounts (such as the rate of change in heart rate) of the resident at sleeping and rising are calculated. As required, these values are calculated for each environment (such as the month, the day in the week, the time, and the weather) at rising.

A comparator 54 compares the physiological data at rising and sleeping which are detected by the biosensors 20, with the average physiological indices and the feature amounts. An audio signal is generated on the basis of a result of this comparison. Consequently, it is possible to supply an audio signal which is optimum to the physiological state of the resident at rising and sleeping.

A specific example will be described. Yesterday, the weather in the daytime was not fine, Mr. A slowly acted in the amusement hall, and a light sleep was detected. From results of past physiological data of Mr. A at sleeping, the average physiological information data of the database show that, when the weather is fine, Mr. A is in good spirits and vigorously acts in the amusement hall, with the result that Mr. A sleeps deeply. Based on the average physiological indices of Mr. A and physiological data of the feature amounts, when the weather is not fine, for example, a lilting audio signal can be supplied to Mr. A in the amusement hall, and effective sound causing a quiet sleep state can be reproduced at sleeping so that Mr. A is induced to a quiet sleep state.

In the case where the average physiological indices and the feature amounts of Mr. A during action show that, when Mr. A has slept deeply, Mr. A slowly acts after rising, a comfortable audio signal is supplied at rising, whereby the psychological and physiological states can be adjusted so that Mr. A acts vigorously.

The calculation unit 51 of the data processing unit 50 calculates average variation (rhythm of variation) of physiological indices of a resident due to the passage of time, and accumulates it in the database.

Specifically, feature amounts (the period, the amplitude, etc.) of variation due to the passage of time are calculated for each of periods such as the whole of a weekday, the whole of a holiday, one week, one month, and one year. If the rhythm of variation of physiological data during a certain period is largely different from the rhythm registered in the database, it can be estimated that the health state and the habit of life of the resident are largely changed from the former ones.

The comparator 54 compares the temporal change of the physiological data obtained from the physiological data which are detected by the biosensors 20, with the average rhythm of variation. Audio signal information is generated on the basis of a result of this comparison. As a result, it is possible to supply an audio signal corresponding to the rhythm of living of the resident which is varied in accordance with the time and the weather including the temperature, the humidity, and the atmospheric pressure.

Figure 5:
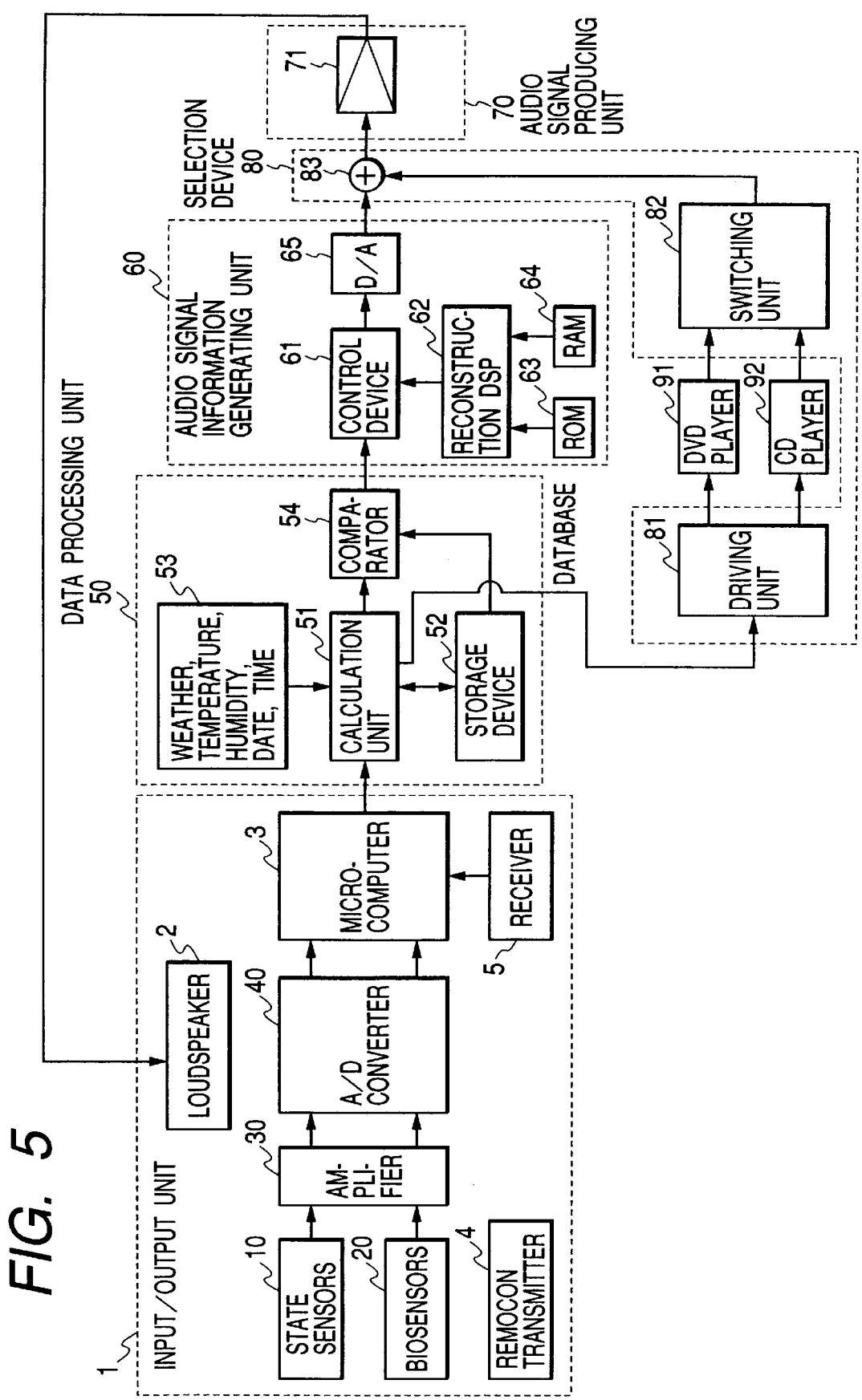
FIG. 5 is a block diagram of an audio apparatus of a third embodiment of the invention.

FIG. 5 is a block diagram of an audio apparatus of a third embodiment of the invention.

In the audio apparatus of the third embodiment, the above-described audio apparatuses of the first and second embodiments are modified so that the audio apparatus further comprises a selection device serving as selecting means for selecting various audio signals.

The selection device 80 comprises: a driving unit 81 which drives various audio devices in accordance with the control signal from the calculation unit 51 of the data processing unit 50; a switching unit 82 which switches over audio signals output from the audio devices; and an adder 83 which adds an audio signal output from the audio signal information generating unit 60 to an audio signal output from one of the audio devices.

In accordance with the control signal from the calculation unit 51, the driving unit 81 of the selection device 80 controls the music piece selection, the reproduction, and the stop of the audio devices such as a DVD player 91 and a CD player 92. The switching unit 82 is switched to the output of the audio device which is selected in accordance with the control signal supplied from the calculation unit 51, so as to supply the audio signal output from the audio device to the adder 83.

The adder 83 adds the audio signal output from the audio signal information generating unit 60 to an audio signal output from one of the audio devices, and supplies the addition result to the audio signal producing unit 70.

The audio signal selected by the selection device 80 is supplied to the audio signal producing unit 70 to be amplified by the amplifier 71. The amplified signal is supplied to the loudspeaker 2 of each room.

The audio signals recorded on recording media of the audio devices can be switched over through the remote-control transmitter 4 which is disposed in each room.

Figure 6A:
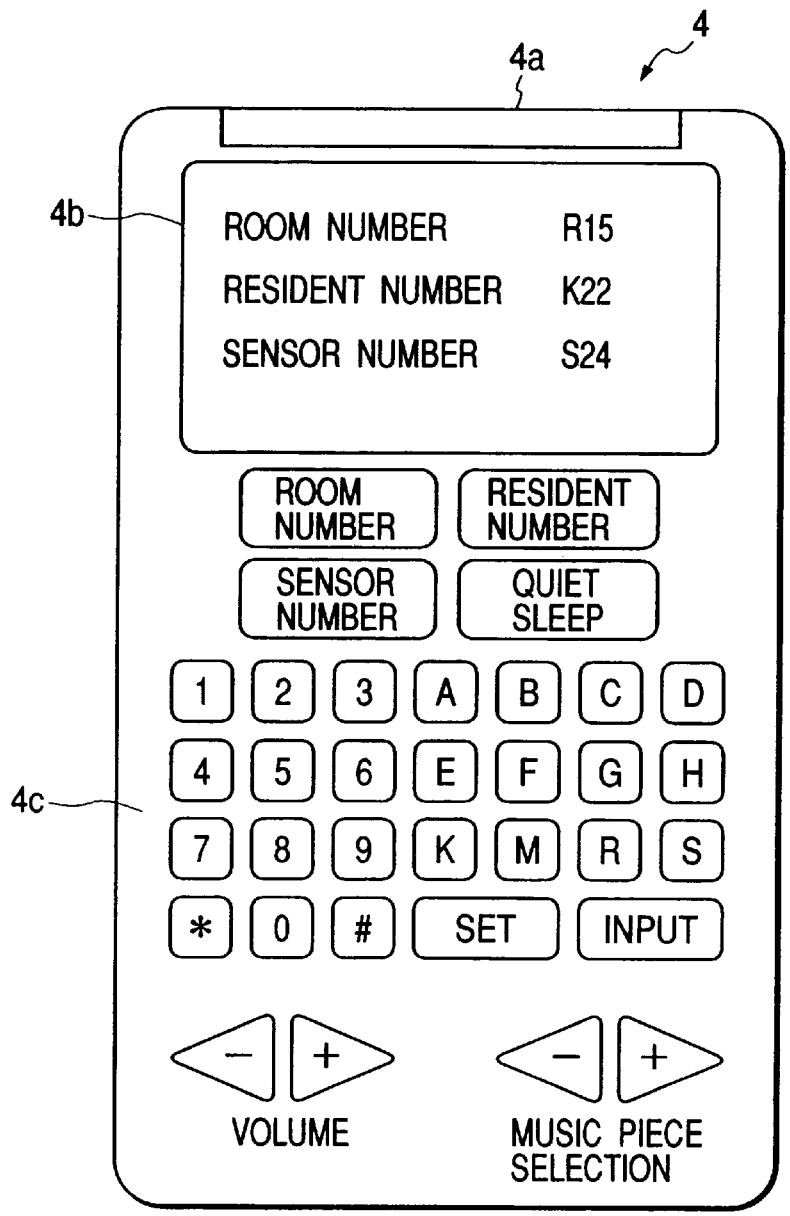
FIGS. 6A and 6B are external view of a remote-control transmitter which is used in the audio apparatus of the invention.
Figure 6B:
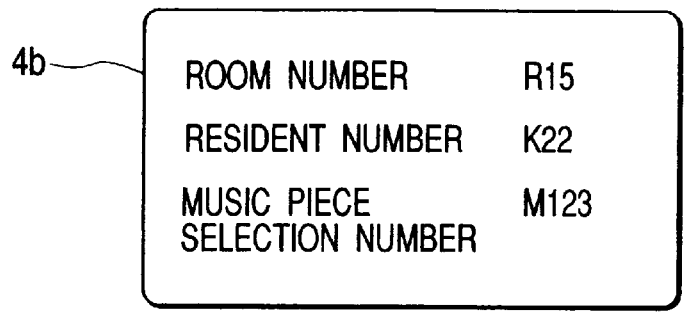

FIG. 6A is an external view of the remote-control. transmitter 4 which is always disposed in each room, and FIG. 6B shows a display form of a display unit.

As illustrated, the remote-control transmitter 4 comprises an infrared emitting unit 4a, and the display unit 4b, and an operating unit 4c having numeral, character keys, etc.

The remote-control transmitter 4 is operated by a resident by oneself, or by a caregiver in place of the resident.

When a sensor attached to a resident is to be registered, for example, a caregiver presses a room number key of the operating unit 4c, and characters indicative of the room number are then displayed on the display unit 4b. Thereafter, the room number of the resident, for example, R15 is input by using character and numeral keys. Similarly, a resident number key is depressed, and the resident number, for example, K22 is then input. After a sensor number key is pressed, the sensor number, for example, S24 is input. Finally, a set key of the operating unit 4c is pressed, so that the data are transmitted via the infrared emitting unit 4a of the remote-control transmitter 4.

Infrared rays emitted from the remote-control transmitter 4 are received by the remote-control receiver 5, and the output data such as the room number (R15), the resident number (K22), and the sensor number (S24) are supplied to the microcomputer 3.

The microcomputer 3 supplies by cable or wireless the output data from the remote-control receiver 5, and various digital data consisting of the output data of the state sensors 10 and the biosensors 20, to the data processing unit 50 in the control room.

The remote-control transmitter 4 can select the audio signals recorded on recording media of the audio device.

When a resident wishes to listen a desired audio signal as BGM during reading, for example, the room. number and the resident number are input in the same manner as described above, and the input key is then pressed. Thereafter, a selected music piece number, for example, M123 is input and the set key is operated. As a result, the desired music piece number is sent to the data processing unit 50.

The calculation unit 51 of the data processing unit 50 registers the supplied digital data in the database for each resident, with correlating the data with the date and time data, and the weather data such as the temperature, the humidity, and the atmospheric pressure.

On the basis of the output data supplied from the remote-control receiver 5, the calculation unit 51 controls the driving unit 81 of the selection device 80 so as to drive the audio device storing the selected music piece (M123) to reproduce the music piece of M123.

At the same time, the calculation unit controls the switching unit 82 so as to select the output of the audio device in which the desired music piece is housed. The audio signal reproduced from the audio device is supplied via the adder 83 to the audio signal producing unit 70 to be amplified by the amplifier 71. Thereafter, the music piece of M123 is output from the loudspeaker 2 of the room of the room number R15.

The resident can change the volume of the loudspeaker 2 by operating a plus or minus key in a volume key of the remote-control transmitter 4. The resident can select a desired music piece by the above-mentioned registering method using the number of the selected music piece, and also by the following method. When a plus or minus key in a music selection key is operated, titles of plural music pieces which are registered in the remote-control. transmitter 4 are sequentially displayed. After one of the titles is selected, the set key is pressed. As a result, the desired music piece is selected.

When the resident wishes to reproduce an audio signal for a quiet sleep during sleeping, a quiet sleep key and the set key are pressed. Based on the personal physiological data for a quiet sleep which are already accumulated in the data base, the calculation unit 51 of the data processing unit 50 then supplies the control signal to the audio signal information generating unit 150 so that audio signal information for a quiet sleep is generated by the audio signal information generating unit 60. The audio signal information output from the audio signal information generating unit 60 is supplied to the audio signal producing unit 70. The signal of the audio signal producing unit is amplified by the amplifier 71. The amplified signal is output from the loudspeaker 2.

The data of the selected music piece which are sent from the remote-control transmitter 4 as a result of an operation by the resident or the caregiver are stored and accumulated in the database of the data processing unit 50, as plural feature data and/or content data of the resident and with being correlated with personal physiological information of the resident.

When vital information supplied from a resident is detected, therefore, the data processing unit 50 can refer the personal feature data and/or content data of the resident which are accumulated in the database, and generate an audio signal corresponding to vital information of the resident. When it is judged that the resident is reading a book while sitting in the chair, for example, a music piece which was desired most frequently under the same state is selected, and the music piece is supplied as an audio signal.

Furthermore, external data such as the time and the weather when a resident selects a desired music piece, the state data of the resident, and the state data and vital information before and after the selection may be stored and accumulated in the database of the data. processing unit 50, with being correlated with each other. In this case, it is possible to supply an audio signal which corresponds more closely to the physiological and psychological states of the resident.

The data processing unit 50 compares the obtained vital information with the plural feature data and/or content data accumulated in the database, causes learning means (for updating or supplementing data so that vital information is always improved) to learn the data, and rewrites the feature data and/or content data, thereby enabling an optimum audio signal based on optimum feature data and/or content data which are obtained by the learning means for newly detected vital information, to be supplied.

As described above, in the audio apparatus of the invention, the disposition of various biosensors and state sensors allows vital information, state data, and action form data of a resident to be detected, and hence these data are accumulated in the database. Furthermore, external data such as the time and the weather are stored and accumulated in the database, with being correlated with vital information, state data, and action form data of a resident.

When vital information of a resident is detected, air optimum audio signal is supplied on the basis of state data and action form data originated from the resident, and the supplied audio signal information is accumulated in the database with being correlated with the above-mentioned various data. According to this configuration, average physiological indices, feature amounts, and average rhythm of variation of the resident can be calculated from various data accumulated in the database, and various obtained data can be learned.

When vital information of a resident is detected, therefore, it is possible to refer the database and send to the resident an audio signal which is optimum to state data and action form data of the resident.

In the above-described audio apparatus of the invention, an audio signal is supplied to a resident. Alternatively, a television set may be disposed in each room, and, in response to a request of a resident, a TV image may be supplied. In the alternative, information of a TV image which is selected by a resident is accumulated as audio signal information in the database.

In the above, the example in which the audio apparatus is used in an asylum for the aged has been described. It is a matter of course that the same effect can be attained also in the case where the audio apparatus is used in a usual home.

As described above, according to the audio apparatus of the invention, audio signal information which is requested physiologically or psychologically by a resident under every situations including the state and action form of the resident, and the external environment such as the time and the weather is accumulated, analyzed, and processed, so that an optimum audio signal can be supplied.

What is claimed is:

1. An audio apparatus comprising:
    vital information detecting means for detecting vital information of a resident;
    a database which is configured by information based on the vital information, and in which at least vital information of the resident is accumulated;
    audio signal information generating means for, when vital information is detected by said vital information detecting means, referring to the vital information of said database, and for generating predetermined audio signal information at the detection; and
    audio signal producing means for producing an audio signal to the resident, said audio signal being based on the audio signal information generated by said audio signal information generating means.

2. An audio apparatus comprising:
    a database in which, when a resident is in one of predetermined states, audio signal information. corresponding to the state is accumulated for the state and for the resident;
    state detecting means for detecting a state of the resident;
    audio signal information generating means for, when the state of the resident is detected by said state detecting means, referring to the audio signal information of said database, and for generating predetermined audio signal information; and
    audio signal producing means for producing an audio signal to the resident, said audio signal being based on the audio signal information generated by said audio signal information generating means.

3. An audio apparatus comprising:
    vital information detecting means for detecting vital information of a resident;
    a database which is configured by information based on the vital information, and in which at least vital information of the resident and audio signal information are accumulated for each of the states and for the resident, the audio signal information corresponding to the state;
    audio signal information generating means for, when vital information is detected by said vital information detecting means, referring to the vital information and the audio signal information of said database, and for generating audio signal information which is optimum in. a state at the detection; and
    audio signal producing means for producing an audio signal to the resident, said audio signal being based on the audio signal information.

4. The audio apparatus according to claim 1, wherein said apparatus further comprises:
    action form detecting means for detecting an action form of the resident, and
    said audio signal information generating means generates audio signal information corresponding also to the action form which is detected by said action for: detecting means.

5. The audio apparatus according to claim 2, wherein said apparatus further comprises:
    action form detecting means for detecting an action form of the resident, and
    said audio signal information generating means generates audio signal information corresponding also to the action form which is detected by said action for: detecting means.

6. The audio apparatus according to claim 3, wherein said apparatus further comprises:
    action form detecting means for detecting an action form of the resident, and
    said audio signal information generating means generates audio signal information corresponding also to the action form which is detected by said action form detecting means.

7. The audio apparatus according to claim 4, wherein said action form detecting means detects whether one person exists in a room or plural persons exist in the room.

8. The audio apparatus according to claim 5, wherein said action form detecting means detects whether one person exists in a room or plural persons exist in the room.

9. The audio apparatus according to claim 6, wherein said action form detecting means detects whether one person exists in a room or plural persons exist in the room.

10. The audio apparatus according to claim 4, wherein said action form detecting means detects whether a person in a room is still or moving.

11. The audio apparatus according to claim 5, wherein said action form detecting means detects whether a person in a room is still or moving.

12. The audio apparatus according to claim 6, wherein said action form detecting means detects whether a person in a room is still or moving.

13. The audio apparatus according to claim 4, wherein said action form detecting means detects whether a person in a room is conducting a predetermined work or not.

14. The audio apparatus according to claim 5, wherein said action form detecting means detects whether a person in a room is conducting a predetermined work or not.

15. The audio apparatus according to claim 6, wherein said action form detecting means detects whether i: person in a room is conducting a predetermined work or not.

16. The audio apparatus according to claim 4, wherein said action form detecting means detects whether em person in a room is in an utterance state or not.

17. The audio apparatus according to claim 5, wherein said action form detecting means detects whether ai person in a room is in an utterance state or not.

18. The audio apparatus according to claim 6, wherein said action form detecting means detects whether a person in a room is in an utterance state or not.

19. The audio apparatus according to claim 1, wherein said vital information detecting means includes ai sensor attached to bedding, said sensor detects physiological data such as an electrocardiographic wave of the resident at sleeping, together with the physiological data, external data such as data of a date, a time, and weather when the physiological data are detected are accumulated in said database, physiological indices relating to physiological information of the resident at rising and sleeping are calculated on the basis of the accumulated data, and accumulated in said database, and feature amounts of the resident at rising and sleeping and obtained from the physiological indices are registered in said database.

20. The audio apparatus according to claim 3, wherein said vital information detecting means includes a sensor attached to bedding, said sensor detects physiological data such as an electrocardiographic wave of the resident at sleeping, together with the physiological data, external data such as data of a date, a time, and weather when the physiological data are detected are accumulated in said database, physiological indices relating to physiological information of the resident at rising and sleeping are calculated on the basis of the accumulated data, and accumulated in said database, and feature amounts of the resident at rising and sleeping and obtained from the physiological indices are registered in said database.

21. The audio apparatus according to claim 19, wherein said apparatus further comprises:

comparing means for comparing the physiological data at rising and sleeping and detected by said sensor, with the average physiological indices and feature amounts, and said audio signal information generating means generates audio signal information on the basis of a result of the comparison.

22. The audio apparatus according to claim 20, wherein said apparatus further comprises:

comparing means for comparing the physiological data at rising and sleeping and detected by said sensor, with the average physiological indices and feature amounts, and said audio signal information generating means generates audio signal information on the basis of a result of the comparison.

23. The audio apparatus according to claim 1, wherein said vital information detecting means includes a sensor for detecting physiological data of the resident during action, physiological data of the resident during action are detected by said sensor, together with the physiological data, external data such as data of a date, a time, and weather when the physiological data are detected are accumulated in said database, physiological indices relating to average physiological information of the resident during action are calculated on the basis of the accumulated data, and accumulated in said database, and feature amounts of the resident during action and obtained from the physiological indices are registered in said database.

24. The audio apparatus according to claim 3, wherein said vital information detecting means includes a sensor for detecting physiological data of the resident during action, physiological data of the resident during action are detected by said sensor, together with the physiological data, external data such as data of a date, a time, and weather when the physiological data are detected are accumulated in said database, physiological indices relating to average physiological information of the resident during action are calculated on the basis of the accumulated data, and accumulated in said database, and feature amounts of the resident during action and obtained from the physiological indices are registered in said database.

25. The audio apparatus according to claim 23, wherein said apparatus further comprises:

comparing means for comparing the physiological data. during action and detected by said sensor, with the physiological indices and feature amounts, and said audio signal information generating means generates audio signal information on the basis of a result of the comparison.

26. The audio apparatus according to claim 24, wherein said apparatus further comprises:

comparing means for comparing the physiological data during action and detected by said sensor, with the physiological indices and feature amounts, and said audio signal information generating means generates audio signal information on the basis of a result of the comparison.

27. The audio apparatus according to claim 1, wherein said vital information detecting means includes a sensor for detecting physiological data of the resident at rest, physiological data of the resident at rest are detected by said sensor, together with the physiological data, external data such as data of a date, a time, and weather when the physiological data are detected are accumulated in said database, physiological indices relating to physiological information of the resident at rest are calculated on the basis of the accumulated data, and accumulated in said database, and feature amounts of the resident at rest and obtained from the physiological indices are registered in said database.

28. The audio apparatus according to claim 3, wherein said vital information detecting means includes a sensor for detecting physiological data of the resident at rest, physiological data of the resident at rest are detected by said sensor, together with the physiological data, external data such as data of a date, a time, and weather when the physiological data are detected are accumulated in said database, physiological indices relating to physiological information of the resident at rest are calculated on the basis of the accumulated data, and accumulated in said database, and feature amounts of the resident at rest and obtained from the physiological indices are registered in said database.

29. The audio apparatus according to claim 27, wherein said apparatus further comprises comparing means for comparing the physiological data at rest and detected by said sensor, with the physiological indices and feature amounts, and said audio signal information generating means generates audio signal information on the basis of a result of the comparison.

30. The audio apparatus according to claim 28, wherein said apparatus further comprises comparing means for comparing the physiological data at rest and detected by said sensor, with the physiological indices and feature amounts, and said audio signal information generating means generates audio signal information on the basis of a result of the comparison.

31. The audio apparatus according to claim 19, wherein said apparatus further comprises:

means for calculating rhythm of variation relating to the resident, from the physiological data accumulated in said database; and comparing means for comparing a temporal change of physiological data obtained from the physiological data detected by said sensor, with the rhythm of variation, and said audio signal information generating means generates audio signal information on the basis of a result of the comparison.

32. The audio apparatus according to claim 20, wherein said apparatus further comprises:

means for calculating rhythm of variation relating to the resident, from the physiological data accumulated in said database; and comparing means for comparing a temporal change of physiological data obtained from the physiological data detected by said sensor, with the rhythm of variation, and said audio signal information generating means generates audio signal information on the basis of a result of the comparison.

33. The audio apparatus according to claim 23, wherein said apparatus further comprises:

means for calculating rhythm of variation relating to the resident, from the physiological data accumulated in said database; and comparing means for comparing a temporal change of physiological data obtained from the physiological data detected by said sensor, with the rhythm of variation, and said audio signal information generating means generates audio signal information on the basis of a result of the comparison.

34. The audio apparatus according to claim 24, wherein said apparatus further comprises:

means for calculating rhythm of variation relating to the resident, from the physiological data accumulated in said database; and comparing means for comparing a temporal change of physiological data obtained from the physiological data detected by said sensor, with the rhythm of variation, and said audio signal information generating means generates audio signal information on the basis of a result of the comparison.

35. The audio apparatus according to claim 27, wherein said apparatus further comprises:

means for calculating rhythm of variation relating to the resident, from the physiological data accumulated in said database; and comparing means for comparing a temporal change of physiological data obtained from the physiological data detected by said sensor, with the rhythm of variation, and said audio signal information generating means generates audio signal information on the basis of a result of the comparison.

36. The audio apparatus according to claim 28, wherein said apparatus further comprises:

means for calculating rhythm of variation relating to the resident, from the physiological data accumulated in said database; and comparing means for comparing a temporal change of physiological data obtained from the physiological data detected by said sensor, with the rhythm of variation, and said audio signal information generating means generates audio signal information on the basis of a result of the comparison.

37. An audio apparatus comprising:

vital information detecting means for detecting vital information of a resident;

audio signal producing means for producing plural audio signals of feature data and/or content data;

selecting means for selecting a desired audio signal from said audio signal producing means; and a database in which, when the resident selects an audio signal through said selecting means, feature data and/or content data of said audio signal, and the vital information detected by said vital information detecting means are accumulated; wherein said audio signal producing means refers, when vital information of the resident is detected by said vital information detecting means, to said database, and produces an audio signal corresponding to the vital information.

38. The audio apparatus according to claim 37, wherein when the resident selects a desired audio signal through said selecting means, external data such as data of a time and weather, and data relating to a state of the resident, and the state and vital information of the resident before and after the selection are accumulated in said database, and said audio signal producing means produces an audio signal which is optimum under a predetermined condition including the detected vital information.

39. An audio apparatus comprising:

vital information detecting means for detecting vital information of a resident;

audio signal producing means for producing plural audio signals of feature data and/or content data;

a database in which vital information which is detected by vital information detecting means of the resident when plural audio signals of feature data and/or content data are produced is accumulated together with the feature data and/or the content data; and learning means for referring to said database, and for learning an audio signal of optimum feature data and/or content data corresponding to vital information, wherein said audio signal producing means produces an audio signal of optimum feature data and/or content data obtained by said learning means, to the detected vital information.

40. The audio apparatus according to claim 39, wherein external data such as data of a time and weather and data relating to a state of the resident when the plural audio signals of feature data and/or content data are produced, and the state and vital information of the resident before and after the detection are accumulated in said database, and said learning means refers to said database and learns an audio signal of optimum feature data and/or content data and corresponding to vital information, a time, weather, and the state of the resident before and after the detection.

41. The audio apparatus according to claim 21, wherein said audio signal producing means produces the audio signal when the resident is to be induced to rise.

42. The audio apparatus according to claim 21, wherein said audio signal producing means produces the audio signal when the resident is to be induced to sleep.

43. The audio apparatus according to claim 22, wherein said audio signal producing means produces the audio signal when the resident is to be induced to rise.

44. The audio apparatus according to claim 22, wherein said audio signal producing means produces the audio signal when the resident is to be induced to sleep.

* * * * *